(12) United States Patent
Sommerich

(10) Patent No.: US 6,916,310 B2
(45) Date of Patent: Jul. 12, 2005

(54) PERCUTANEOUS ACCESS DEVICE

(75) Inventor: Bob Sommerich, Norton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 102 days.

(21) Appl. No.: 10/449,179

(22) Filed: May 30, 2003

(65) Prior Publication Data
US 2004/0243064 A1 Dec. 2, 2004

(51) Int. Cl.$^7$ .......................... A61M 5/32; A61M 5/178; A61M 25/00
(52) U.S. Cl. .................. 604/175; 604/164.04; 604/174; 604/265
(58) Field of Search .................. 604/264, 265, 604/27, 30, 164.01, 164.02, 167.01, 167.02, 167.03, 167.04, 167.06, 174–175, 164.04

(56) References Cited

U.S. PATENT DOCUMENTS

| | | | |
|---|---|---|---|
| 4,676,782 A | * | 6/1987 | Yamamoto et al. ......... 604/175 |
| 4,915,694 A | * | 4/1990 | Yamamoto et al. ......... 604/180 |
| 4,917,686 A | * | 4/1990 | Bayston et al. ............. 604/265 |
| 4,959,054 A | | 9/1990 | Heimke |
| 5,098,398 A | | 3/1992 | Lundgren |
| 5,234,408 A | | 8/1993 | Griffith |
| 5,391,156 A | * | 2/1995 | Hildwein et al. ........... 604/174 |
| 5,728,103 A | | 3/1998 | Picha |
| 5,766,249 A | | 6/1998 | Griffith |
| 5,792,119 A | * | 8/1998 | Marx ......................... 604/247 |
| 5,820,607 A | | 10/1998 | Tcholakian et al. |
| 5,830,191 A | | 11/1998 | Hildwein et al. |
| 5,833,666 A | * | 11/1998 | Davis et al. ................ 604/180 |
| 6,017,355 A | | 1/2000 | Hessel et al. |
| 6,099,508 A | | 8/2000 | Bousquet |
| 6,306,114 B1 | | 10/2001 | Freeman et al. |

FOREIGN PATENT DOCUMENTS

| | | |
|---|---|---|
| DE | 20012624 U | 10/2000 |
| EP | 0134340 | 3/1985 |

* cited by examiner

Primary Examiner—Nicholas D. Lucchesi
Assistant Examiner—Catherine S. Williams
(74) Attorney, Agent, or Firm—Nutter, McClennen & Fish, LLP

(57) ABSTRACT

A percutaneous access device is provided including a sleeve having an inner lumen extending therethrough that is adapted to slidably receive a catheter, and at least one flange disposed around the sleeve and adapted to be positioned adjacent a tissue surface. In a preferred embodiment, the device includes a first flange disposed around the sleeve and adapted to be positioned adjacent a first tissue surface, and a second flange disposed around the sleeve and spaced apart from the first flange such that the second flange is adapted to be disposed adjacent a second tissue surface opposed to the first tissue surface. In use, the flanges 16, 18 are positioned on opposed sides of tissue so that the device 10 is effective to prevent tissue surrounding the percutaneous access device from coming into contact with the catheter as it is introduced through the sleeve 12. The device also includes an antimicrobial agent that is effective to protect against bacterial colonization on and around the access device, the catheter, and the tissue surface surrounding the access device.

31 Claims, 2 Drawing Sheets

US 6,916,310 B2

PERCUTANEOUS ACCESS DEVICE

FIELD OF THE INVENTION

The present invention relates to a percutaneous access device, and in particular to a percutaneous access device that is effective to prevent or reduce the risk of infection in tissue surrounding the percutaneous device.

BACKGROUND OF THE INVENTION

Percutaneous access devices are used to introduce extracorporeal medical devices, such as catheters, through the skin for a variety of purposes, including to transport fluid, conduct diagnostic tests, access blood for dialysis, monitor pressure, and deliver drugs. Hydrocephalus, for example, can require the use of an external ventricular drainage (EVD) catheter to remove fluid from a patient's ventricle. Hydrocephalus is a neurological condition that is caused by the abnormal accumulation of cerebrospinal fluid (CSF) within the ventricles, or cavities, of the brain. CSF is a clear, colorless fluid that surrounds the brain and spinal cord, and that constantly circulates through the ventricular system of the brain and is ultimately absorbed into the bloodstream. Hydrocephalus, which can affect people of any age, but affects mostly infants and young children, arises when the normal drainage of CSF in the brain is blocked in some way. Blockage of the flow of CSF requires an increasing pressure for CSF to be absorbed into the bloodstream. This increasing pressure can interfere with the perfusion of the nervous system. Hydrocephalus can be treated by introducing an EVD catheter through a burr hole in a patient's skull and implanting the catheter in the patient's ventricle.

One common risk associated with the use of many catheters, including ventricular catheters, is the risk of infection at the site of the catheter insertion. Current reported infection rates of EVD catheters range from 1–25%, with the typical rate of approximately 17%. Minimizing or eliminating the risk of infection is critical for devices that contact the brain or cerebrospinal fluid. Current efforts to approach this issue include coating or impregnating the catheter with antibiotics or hydrophilic solutions that do not allow the bacteria to colonize on the surface of the device.

While these devices have proven effective, there remains a need for an improved percutaneous access device to facilitate insertion of a catheter while minimizing or eliminating the potential risk of infections to the tissue surrounding the percutaneous access site.

SUMMARY OF THE INVENTION

In general the present invention provides a percutaneous access device including a tubular sleeve having an inner lumen extending therethrough that is adapted to slidably receive a catheter, and at least one flange disposed around the sleeve and adapted to be positioned adjacent a tissue surface. At least one of the sleeve and the flange(s) include an antimicrobial agent. In a preferred embodiment, the device includes a first flange disposed around the sleeve and adapted to be positioned adjacent a first tissue surface, and a second flange disposed around the sleeve and spaced apart from the first flange such that the second flange is adapted to be disposed adjacent a second tissue surface opposed to the first tissue surface. The second flange is preferably positioned at a distal end of the sleeve, and the first flange is preferably positioned a distance apart from a proximal end of the sleeve to allow a proximal end of the sleeve to be grasped during use. The first and second flanges can extend in a direction substantially transverse to an axis of the sleeve. In use, the sleeve is adapted to slidably and sealingly receive a catheter. In an exemplary embodiment, the percutaneous access device is used with a ventricular catheter.

In another embodiment, a catheter kit is provided including a percutaneous access device having a body with a lumen extending therethrough and adapted to receive a catheter, and at least one tissue-protecting member adapted to protect tissue surrounding the percutaneous access device from coming into contact with a catheter. The percutaneous access device also includes an antimicrobial agent. The kit further includes a catheter adapted to be slidably and sealingly disposed through the lumen in the percutaneous access device.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
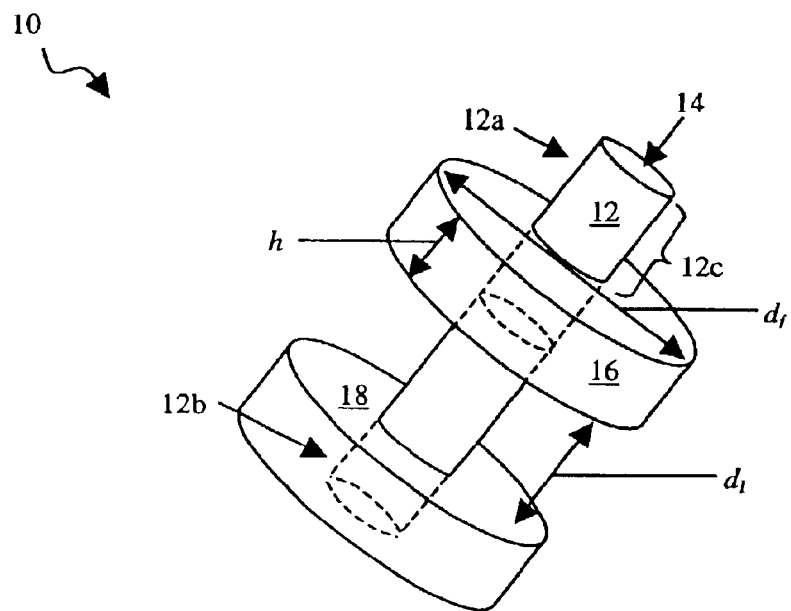
FIG. 1 is a perspective view of an exemplary embodiment of a percutaneous access device according to the present invention.
Figure 2:
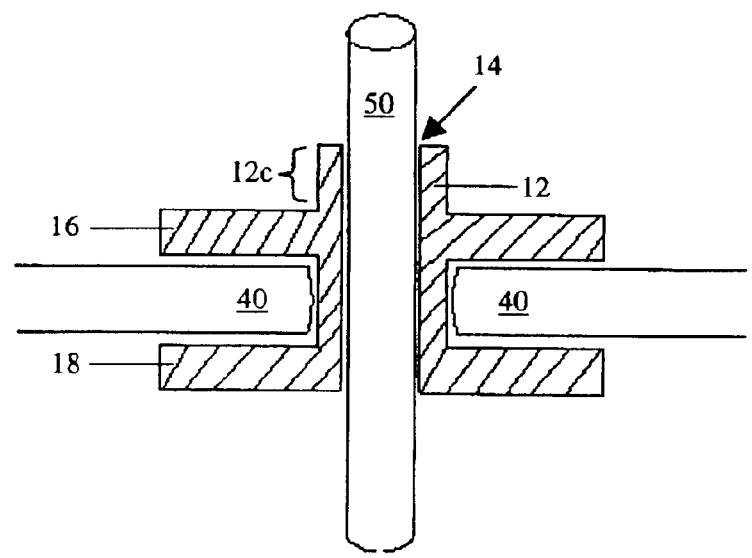
FIG. 2 is a side, sectional view of the percutaneous access device shown in FIG. 1.

As shown in FIGS. 1 and 2, the present invention generally provides a percutaneous access device 10 that is effective for use in inserting a percutaneous device, such as a catheter 50, into a patient. While the device is described and illustrated for use with a ventricular catheter, a person skilled in the art will appreciate that the device can be used for a variety of procedures and with a variety of percutaneous devices, including, for example, urethral, venous, and arterial catheters, orthopaedic trauma pins, intracranial press sensors, and other percutaneous device, including both short-term and long-term devices. In general, the device 10 includes a sleeve 12 having an inner lumen 14 extending therethrough for receiving a catheter 50, and at least one tissue-protecting member disposed around the sleeve 12. As shown in FIGS. 1 and 2, the device 10 includes first and second tissue-protecting members that are in the form of first and second flanges 16, 18 positioned around the sleeve 12 and spaced a distance apart from one another. In use, the flanges 16, 18 are positioned on opposed sides of tissue 40 so that the device 10 is effective to prevent tissue surrounding the percutaneous access device from coming into contact with the catheter inserted through the sleeve 12. The device 10 also includes an antimicrobial agent that is effective to protect against bacterial colonization on and around the access device 10, the catheter 50, and the tissue 40 surrounding the access device 10.

The sleeve 12 can have a variety of shapes and sizes, but should be adapted to receive a catheter 50 or a similar percutaneous delivery or fluid withdrawal device. As shown in FIGS. 1 and 2, the sleeve 12 is substantially cylindrical and includes a proximal end 12a, a distal end 12b, and an inner lumen 14 extending therethrough. The inner lumen 14 of the sleeve 12 is preferably adapted to sealingly, yet slidably receive a catheter 50 therein. The sealing effect can be achieved using a variety of techniques. By way of non-limiting example, the sleeve 12 can have an inner diameter substantially the same as or slightly smaller than a diameter of the catheter 50 adapted to be disposed therein. In order to receive a catheter 50, the sleeve 12 can be formed from a pliable material to allow the sleeve 12 to expand during insertion of the catheter, while providing a fluid-tight seal around a catheter. Alternatively, or in addition, the sleeve 12 can optionally include a longitudinal slit (not shown) to facilitate placement of the catheter 50, or other device, within the sleeve 12. Once the catheter or other device is placed within the sleeve 12, the sleeve would preferably self-close around the catheter to form a tight seal. In another embedment, an expander tool (not shown) can optionally be used to facilitate insertion of the catheter 50 into the sleeve. The expander tool can have virtually any configuration, but should be effective to stretch or expand the inner diameter of the sleeve 12 to allow for insertion of the catheter 50. In an exemplary embodiment, the inner diameter of the sleeve 12 is in the range of about 0.25–10 mm. A person skilled in the art will appreciate that the inner diameter of sleeve can vary based on the intended use. Moreover, the sleeve 12 is not limited to having a cylindrical shape, but rather can be adapted for use with other devices having a variety of shapes and sizes.

Alternatively, or in addition, the inner lumen 14 of the sleeve 12 can include a seal disposed therein. By way of non-limiting example, the seal can be a sheath, web, mesh, or similar type of material disposed around all or a portion of the inner surface of the sleeve 12. Alternatively, the seal can be an annular ring or valve-type member that is preferably disposed adjacent the proximal and distal ends 12a, 12b. A person skilled in the art will appreciate that a variety of techniques can be used to provide a fluid-tight seal around a catheter 50 disposed within the sleeve 12.

The tissue-protecting member(s) 16, 18 also have a variety of configurations, but are preferably disposed around the sleeve 12 and effective to protect the tissue surface surrounding the device 10 from coming into contact with a catheter that is inserted through or disposed within the sleeve 12. The tissue-protecting member can have virtually any shape and size, and can be positioned anywhere along the sleeve 12. Preferably, however, the device 10 includes first and second tissue-protecting members positioned a distance apart from one another to allow tissue 40 to be disposed therebetween. As shown in FIGS. 1 and 2, the tissue-protecting members are in the form of first and second flanges 16, 18 disposed around the sleeve 12 and positioned a distance $d_l$ apart from one another. The first and second flanges 16, 18 can be formed as a unitary construction with the sleeve 12, or one or both of the flanges 16, 18 can be slidably disposed around the sleeve 12 to allow the distance $d_l$ between the flanges 16, 18 to be adjusted as desired. In an exemplary embodiment, the second flange 18 is fixedly positioned at the distal end 12b of the sleeve 12, and the first flange 16 is slidably positioned around the sleeve 12 at a distance from the proximal end 12a of the sleeve 12. The position of the first flange 16 provides a proximal extension portion 12c of the sleeve 12 that can be grasped during use. A person skilled in the art will appreciate that proximal extension portion 12c can be adapted to facilitate grasping and manipulation of the device 10, and thus can include a knurled surface, a handle, or similar features formed thereon or matable thereto.

While each flange 16, 18 can have any shape and size, FIGS. 1 and 2 illustrate substantially cylindrical flanges 16, 18 having a height h and diameter $d_f$, which can vary depending on the intended use. Preferably, the diameter $d_f$ of each flange 16, 18 is sufficient to allow the flanges 16, 18 to cover a surface area of tissue 40 surrounding the device 10 in order to prevent contact between a catheter 50 inserted through the sleeve 12 and the tissue surface 40. The height h of each flange 16, 18 can also vary, but the height h should be sufficient to provide some flexibility, at least to the second flange 18, to allow the device 10 to be implanted through a slit in formed in the tissue, as will be discussed in more detail below. A person skilled in the art will appreciate that the tissue-protecting members can have any shape and size, and that the illustrated flanges 16, 18 are merely exemplary embodiments of one type of a tissue-protecting member.

At least one of the flanges 16, 18 can also include one or more anchor members (not shown) formed thereon or mated thereto for attaching the flange(s) 16, 18 to the tissue surface. The anchor members can be formed on or mated to any portion of the flange(s) 16, 18, and can have a variety of configurations. Preferably, each anchor member is disposed around a periphery of the flange(s) 16, 18. A variety of anchor members can be used including, for example, eyelets, hooks, adhesives, and combinations thereof. In use, each anchor member can be sutured or otherwise attached to the tissue surface to securely attach the device 10 to the tissue surface.

Each component 12, 16, 18 of the device 10 can also be made from a variety of materials, but preferably at least a portion of the device 10 includes an antimicrobial agent. The agent can be coated onto, implanted within, or impregnated within the device 10 using a variety of techniques. In an exemplary embodiment, the sleeve 12 and the first and second flanges 16, 18 are formed from a material capable of being impregnated with an antimicrobial agent. By way of non-limiting example, U.S. Pat. No. 4,917,686 of Bayston et al., which is incorporated herein by reference in its entirety, discloses an antimicrobial medical implant device that exhibits persistent antimicrobial activity, and methods for making the same.

In one embodiment, an antimicrobial agent can be embedded within the percutaneous access device of the invention by subjecting all surfaces of the body of the device (which is made of a polymeric material) to a solution containing (1) a suitable swelling agent (solvent), such as hexane, toluene, xylene or preferably chloroform, and (2) an antimicrobial agent(s) (solute). The swelling agent is effective to increase the intermolecular spaces of the polymer, thereby allowing the solution to penetrate and swell the entire body of polymeric material. As a result, the antimicrobial is dispersed throughout the body of the device within the enlarged intermolecular spaces thereof. The swelling agent is thereafter removed by evaporation to reverse swelling, while allowing the antimicrobial agent(s) to be retained in a substantially uniform dispersion in the intermolecular spaces throughout the body of polymeric material. The molecules of the antimicrobial agent(s) are thus essentially in a solid state solution with the molecules of the body of the polymeric material, and will thereafter migrate toward the surfaces of the device and through the surfaces thereof solely by molecular diffusion. After the swelling agent is removed, the device is suitably sterilized by appropriate known techniques. Typical sterilization methods used for medical devices can be used for the antimicrobial sheath including, for example, steam sterilization.

In use, it is believed that the antimicrobial agent(s) within the body of polymeric material are released to and through the surfaces by solid state diffusion. Because of the molecular structure of the polymer and the intimate molecular association of the antimicrobial agent(s) therewith, the diffusion of these agent(s) occurs at a rate which provides antimicrobial efficacy at the surfaces of the device for a substantial period of time. Thus, surgically implanted silicone elastomer percutaneous access devices, when processed according to the invention, will resist bacterial contamination introduced at the time of surgery which can lead to the colonization of the implant and its ultimate failure, removal and replacement; and will provide longer period of protection against colonization by introduced bacteria due to the constant diffusion of antimicrobial to the surfaces of the device.

In another embodiment, the sleeve 12 and the flanges 16, 18 can include a cavity formed therein for receiving an antimicrobial agent, as disclosed in U.S. Pat. No. 5,820,607 of Tcholakian et al. ("Tcholakian"), which is also incorporated herein by reference in its entirety. A person skilled in the art will appreciate that a variety of techniques can be used to form an antimicrobial device 10 in accordance with the present invention, and that virtually any antimicrobial agent can be used.

A variety of antimicrobial agents can be included with the percutaneous access device of the invention. Exemplary antimicrobial agents for use in making a percutaneous access device in accordance with the present invention include the following: (1) rifampin, which is a semisynthetic antibiotic derivative of rifamycin B (specifically, rifampin is the hydrazone, 3-(4-methyl-1-piperazinyliminomethyl)-rifampinSV.); and (2) clindamycin hydrochloride. The exemplary antimicrobial agents can be used in combination as a solute, which is commercially available under the name BACTISEAL™, manufactured by Codman & Shurtleff, Inc. of Raynham, Mass. Other suitable antimicrobial agents that can be used with the present invention include antibiotics, antifungal, and antiviral agents. Suitable antibiotics include, for example, minocycline, rifampin, penicillins, cephaloporins, monobactams, carbapenems, clindamycin, chloramphenicol, tetracycline, quinolones, macrolides, sulfa antibiotics, trimethoprim, fusidic acid and aminoglycosides. Suitable antiviral agents include, for example, acyclovir, ganciclovir, fosiornet and pencyclovir, and suitable antifungal agents include, for example, amphotericin B, azoles, flucytosine, cilofungin and nikko Z. The percutaneous access device can also optionally include anticoagulants, antifibrin agents, anti-inflammatory agents, and other useful agents not specifically disclosed herein. Suitable anticoagulants include, for example, EGTA, EDTA, heparin, urokinase, streptokinase, and others, and suitable anti-inflammatory agents include steroids, nonsteroidal antiinflammatory agents, and salicylates.

The effective amount of antimicrobial agent(s) employed is dependent upon the size and shape of the particular medical device and upon the kind and wall thicknesses of the selected polymeric material. In the presently preferred embodiments, the amount of antimicrobial agent(s) is preferably about 0.1% to 1.0%, and more preferably is about 0.1% to 0.2%, by weight of each agent to volume of solvent.

Figure 3:
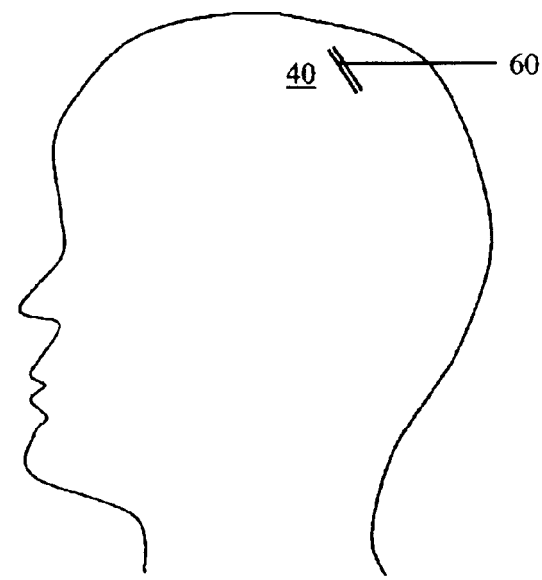
FIG. 3 is an illustration of a patient's head having an incision formed therein for receiving a percutaneous access device.
Figure 4:
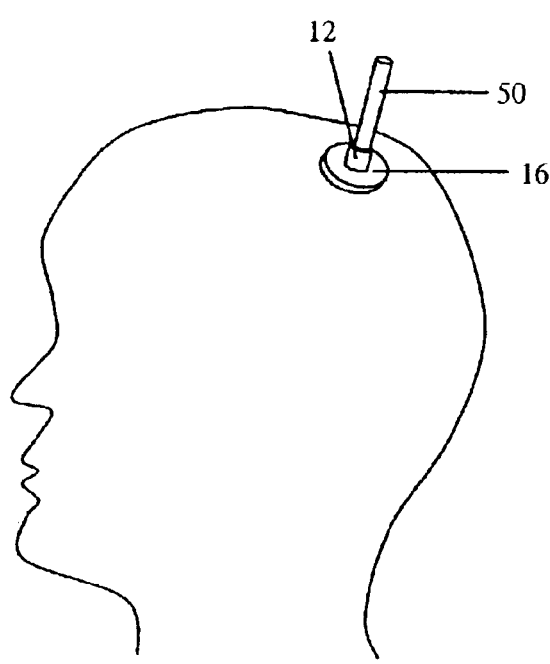
FIG. 4 is an illustration of the patient's head shown in FIG. 3 having the percutaneous access device of FIG. 1 implanted therein.

FIGS. 3–4 illustrate the device 10 in use. As previously stated, the device 10 can be used to introduce a variety of percutaneous devices into a patient's body, but in an exemplary embodiment the device 10 is used to introduce a ventricular catheter 50 through a patient's skull to enable the catheter 50 to be inserted into the patient's ventricles. As shown in FIG. 3, an incision 60 is made in the tissue 40 on the patient's skull. The second flange 18 on the access device 10 is then inserted through the slit to position the second flange 18 underneath and adjacent to the tissue surface, as shown in FIG. 2. Where the first flange 16 is slidable, the proximal portion 12c of the sleeve 12 can be grasped while the first flange 16 is slid toward the second flange 18 and positioned against the opposed tissue surface to sandwich the tissue 40 between the flanges 16, 18. A catheter 50 can then be inserted through the inner lumen 14 in the sleeve 12 to position the catheter 50 as desired. Depending on the configuration of the sleeve 12, an expander tool can be utilized to stretch the sleeve 12 to allow insertion of the catheter 50 therethrough. Once the expander tool is released, the sleeve 12 returns to its original size, whereby the sleeve 12 provides a fluid-tight seal around the catheter 50. The catheter 50 can then be slid with respect to the device 10, as necessary.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A percutaneous access device, comprising:
   a sleeve having an inner lumen extending therethrough that is adapted to slidably receive a catheter; and
   at least one flange slidably formed on the sleeve and adapted to be positioned adjacent a tissue surface;
   wherein the sleeve and at least one flange both include an antimicrobial agent.

2. The percutaneous access device of claim 1, wherein the sleeve includes a first flange disposed around the sleeve and adapted to be positioned adjacent a first tissue surface, and a second flange disposed around the sleeve and spaced apart from the first flange such that the second flange is adapted to be disposed adjacent a second tissue surface opposed to the first tissue surface.

3. The percutaneous access device of claim 2, wherein the second flange is positioned at a distal end of the sleeve, and the first flange is positioned a distance apart from a proximal end of the sleeve to allow a proximal end of the sleeve to be grasped during use.

4. The percutaneous access device of claim 2, wherein the first and second flanges each have a substantially cylindrical shape.

5. The percutaneous access device of claim 2, wherein the first and second flanges extend in a direction substantially transverse to an axis of the sleeve.

6. The percutaneous access device of claim 1, wherein the sleeve is adapted to slidably and sealingly receive a catheter.

7. The percutaneous access device of claim 6, wherein the catheter is selected from the group consisting of a ventricular catheter, a urethral catheter, a venous catheter, and an arterial catheter.

8. The percutaneous access device of claim 6, wherein the inner lumen of the sleeve includes a seal disposed therein and adapted to provide a fluid-tight seal around a catheter member disposed therein.

9. The percutaneous access device of claim 8, wherein the seal is selected from the group consisting of one of more annular rings, a sheath, a web, a clip, and a bonding agent.

10. The percutaneous access device of claim 1, wherein at least one of the sleeve and the at least one flange is formed from a pliable material.

11. The percutaneous access device of claim 10, wherein at least one of the sleeve and the at least one flange is formed from a material selected from the group consisting of silicone and polyurethane.

12. The percutaneous access device of claim 2, wherein one of the flanges and the sleeve are of a unitary construction.

13. The percutaneous access device of claim 1, wherein the antimicrobial agent comprises a coating disposed on a surface of the sleeve and at least one flange.

14. The percutaneous access device of claim 1, wherein the antimicrobial agent is impregnated within the sleeve and the at least one flange.

15. The percutaneous access device of claim 14, wherein the antimicrobial agent comprises a mixture of rifampin and clindamycin hydrochloride.

16. A catheter kit, comprising:
  a percutaneous access device comprising a body having a lumen extending therethrough and adapted to receive a catheter, and at least one tissue-protecting member slidably formed on the body and adapted to protect tissue surrounding the percutaneous access device from coming into contact with a catheter, at least one tissue-protecting member and the body of the percutaneous access device both including an antimicrobial agent; and
  a catheter adapted to be slidably and sealingly disposed through the lumen in the percutaneous access device.

17. The kit of claim 16, wherein the body of the percutaneous access device comprises a sleeve, and the at least one tissue-protecting member comprises at least one flange disposed around the sleeve.

18. The kit of claim 17, wherein percutaneous access device includes a first flange disposed around the sleeve and adapted to be positioned adjacent a first tissue surface, and a second flange disposed around the sleeve and spaced apart from the first flange such that the second flange is adapted to be disposed adjacent a second tissue surface opposed to the first tissue surface.

19. The kit of claim 16, wherein the catheter is a ventricular catheter.

20. The kit of claim 16, wherein the inner lumen of the percutaneous access device includes a seal disposed therein and adapted to provide a fluid-tight seal around the catheter when the catheter is disposed therein.

21. The kit of claim 20, wherein the seal is selected from the group consisting of one of more annular rings, a sheath, a web, a clip, and a bonding agent.

22. The kit of claim 17, wherein at least one of the sleeve and the at least one flange is formed from a pliable material.

23. The kit of claim 17, wherein at least one of the sleeve and the at least one flange is formed from a material selected from the group consisting of silicone and polyurethrane.

24. The kit of claim 18, wherein the body and one of the flanges is of a unitary construction.

25. The kit of claim 16, wherein the antimicrobial agent comprises a coating.

26. The kit of claim 16, wherein the antimicrobial agent is impregnated within at least one tissue-protecting member and the body of the percutaneous access device.

27. A percutaneous access device, comprising:
  a sleeve having an inner lumen extending therethrough that is adapted to slidably receive a catheter; and
  a first flange disposed around the sleeve and adapted to be positioned adjacent a first tissue surface; and
  a second flange slidably disposed around the sleeve and spaced apart from the first flange such that the second flange is adapted to be disposed adjacent a second tissue surface opposed to the first tissue surface;
  wherein both the sleeve and at least one of the flanges includes an antimicrobial agent.

28. The percutaneous access device of claim 27, wherein the first flange is fixedly mated to the sleeve.

29. The percutaneous access device of claim 27, wherein the sleeve and the first flange is of a unitary construction.

30. The percutaneous access device of claim 27, wherein the antimicrobial agent is impregnated within the sleeve and at least one of the first and the second flanges.

31. The percutaneous access device of claim 27, wherein the antimicrobial agent is coated onto the sleeve and at least one of the first and the second flanges.

* * * * *